US010683119B2

(12) United States Patent
Linderman et al.

(10) Patent No.: US 10,683,119 B2
(45) Date of Patent: Jun. 16, 2020

(54) MARKER ELEMENT, DEVICE FOR MAKING A MARKER ELEMENT, AND METHOD FOR MAKING A MARKER ELEMENT

(71) Applicant: MERIT MEDICAL SYSTEMS, INC., South Jordan, UT (US)

(72) Inventors: Evan Linderman, Northbrook, IL (US); Michael Plishka, Lake Villa, IL (US)

(73) Assignee: Merit Medical Systems, Inc., South Jordan, UT (US)

( * ) Notice: Subject to any disclaimer, the term of this patent is extended or adjusted under 35 U.S.C. 154(b) by 30 days.

(21) Appl. No.: 14/286,484

(22) Filed: May 23, 2014

(65) Prior Publication Data
US 2015/0335391 A1 Nov. 26, 2015

(51) Int. Cl.
*A61B 90/00* (2016.01)
*A61B 17/00* (2006.01)
*B65B 55/02* (2006.01)
*B65B 5/06* (2006.01)

(52) U.S. Cl.
CPC ............. *B65B 55/02* (2013.01); *A61B 90/39* (2016.02); *B65B 5/06* (2013.01); *A61B 2017/00526* (2013.01); *A61B 2090/3925* (2016.02); *A61B 2090/3954* (2016.02); *A61B 2090/3966* (2016.02); *A61B 2090/3987* (2016.02); *Y10T 29/49909* (2015.01); *Y10T 29/53987* (2015.01)

(58) Field of Classification Search
CPC ......... A61B 19/54; A61B 90/00; A61B 90/39; A61B 2090/3925; A61B 2090/3954; A61B 2090/3966; A61B 2090/3987; B65B 55/02; B65B 5/06; Y10T 29/53987; Y10T 29/49909
See application file for complete search history.

(56) References Cited

U.S. PATENT DOCUMENTS 5,902,310 A 5/1999 Foerster et al.
5,941,890 A 8/1999 Voegele et al.
(Continued)

FOREIGN PATENT DOCUMENTS

WO WO 2007/094001 A2 8/2007
WO WO 2013/112944 A1 8/2013

OTHER PUBLICATIONS

International Search Report issued in PCT/2015/032012 dated Mar. 29, 2016.

*Primary Examiner* — Jeffrey G Hoekstra
*Assistant Examiner* — Patrick M Mehl
(74) *Attorney, Agent, or Firm* — Stoel Rives LLP

(57) ABSTRACT

Disclosed are devices, kits and methods for forming a marker element including, in aspects, a tube having a longitudinal direction, a base element received in a first end of the tube, a wire receiving portion at a second end of the tube, a force applicator receivable within the second end of the tube, the force applicator being configured to apply force to a received wire in the longitudinal direction of the tube to deformably compress the received wire to a selected length relative to the longitudinal direction of the tube. Also disclosed is a marker delivery device having a tube, a marker element preformed within the tube, and an actuator element receivable in the tube to move the marker element from the tube into a tissue site.

36 Claims, 7 Drawing Sheets

(56) References Cited

U.S. PATENT DOCUMENTS

| | | | |
|---|---|---|---|
| 6,116,890 A * | 9/2000 | Sors | B30B 11/02 |
| | | | 425/352 |
| 6,220,248 B1 | 4/2001 | Voegele et al. | |
| 6,228,055 B1 | 5/2001 | Foerster et al. | |
| 6,261,302 B1 | 7/2001 | Voegele et al. | |
| 6,270,464 B1 | 8/2001 | Fulton, III et al. | |
| 6,347,241 B2 | 2/2002 | Burbank et al. | |
| 6,356,782 B1 | 3/2002 | Sirimanne et al. | |
| 6,371,904 B1 | 4/2002 | Sirimanne et al. | |
| 6,425,903 B1 | 7/2002 | Voegele | |
| 6,432,064 B1 | 8/2002 | Hibner et al. | |
| 6,547,824 B1 * | 4/2003 | Price | A61F 2/30767 |
| | | | 623/18.11 |
| 6,575,991 B1 | 6/2003 | Chesbrough et al. | |
| 6,605,047 B2 | 8/2003 | Zarins et al. | |
| 6,662,041 B2 | 12/2003 | Burbank et al. | |
| 6,725,083 B1 | 4/2004 | Burbank et al. | |
| 6,766,186 B1 | 7/2004 | Hoyns et al. | |
| 6,993,375 B2 | 1/2006 | Burbank et al. | |
| 6,996,433 B2 | 2/2006 | Burbank et al. | |
| 7,044,957 B2 | 5/2006 | Foerster et al. | |
| 7,047,063 B2 | 5/2006 | Burbank et al. | |
| 7,083,576 B2 | 8/2006 | Zarins et al. | |
| 7,229,417 B2 | 6/2007 | Foerster et al. | |
| 7,465,279 B2 | 12/2008 | Beckman et al. | |
| 7,565,191 B2 | 7/2009 | Burbank et al. | |
| 7,569,065 B2 | 8/2009 | Chesbrough et al. | |
| 7,625,397 B2 | 12/2009 | Foerster et al. | |
| 7,651,505 B2 | 1/2010 | Lubock et al. | |
| 7,668,582 B2 | 2/2010 | Sirimanne et al. | |
| 7,783,336 B2 | 8/2010 | MacFarlane et al. | |
| 7,945,307 B2 | 5/2011 | Lubock et al. | |
| 7,970,454 B2 | 6/2011 | Jones et al. | |
| 8,052,708 B2 | 11/2011 | Chesbrough et al. | |
| 8,060,183 B2 | 11/2011 | Leopold et al. | |
| 8,064,987 B2 | 11/2011 | Carr, Jr. | |
| 8,068,895 B2 | 11/2011 | Speeg et al. | |
| 8,079,964 B2 | 12/2011 | Reichel et al. | |
| 8,224,424 B2 | 7/2012 | Burbank et al. | |
| 8,241,299 B2 | 8/2012 | Hibner | |
| 8,277,391 B2 | 10/2012 | Foerster et al. | |
| 8,306,602 B2 | 11/2012 | Sirimanne et al. | |
| 8,311,610 B2 | 11/2012 | Ranpura | |
| 8,320,993 B2 | 11/2012 | Sirimanne et al. | |
| 8,320,994 B2 | 11/2012 | Sirimanne et al. | |
| 8,361,082 B2 | 1/2013 | Jones et al. | |
| 8,371,443 B2 | 2/2013 | Nock et al. | |
| 8,401,622 B2 | 3/2013 | Talpade et al. | |
| 8,437,834 B2 | 5/2013 | Carr, Jr. | |
| 8,498,693 B2 | 7/2013 | Jones et al. | |
| 8,529,465 B2 | 9/2013 | Speeg et al. | |
| 8,532,747 B2 | 9/2013 | Nock et al. | |
| 8,579,931 B2 | 11/2013 | Chesbrough et al. | |
| 2003/0233101 A1 * | 12/2003 | Lubock | A61M 37/0069 |
| | | | 606/116 |
| 2005/0228311 A1 * | 10/2005 | Beckman | A61B 90/39 |
| | | | 600/567 |
| 2006/0079805 A1 * | 4/2006 | Miller | A61B 90/39 |
| | | | 600/562 |
| 2008/0033286 A1 | 2/2008 | Whitmore et al. | |
| 2008/0058769 A1 | 3/2008 | Naslund | |
| 2008/0125766 A1 | 5/2008 | Lubock et al. | |
| 2008/0188768 A1 | 8/2008 | Zarins et al. | |
| 2009/0018439 A1 | 1/2009 | Jones et al. | |
| 2009/0048610 A1 * | 2/2009 | Tolkowsky | A61B 90/11 |
| | | | 606/130 |
| 2009/0088665 A1 | 4/2009 | Beckman et al. | |
| 2009/0131734 A1 * | 5/2009 | Neustadter | A61N 5/1049 |
| | | | 600/8 |
| 2009/0131825 A1 | 5/2009 | Burbank et al. | |
| 2009/0216150 A1 | 8/2009 | Reichel et al. | |
| 2009/0216181 A1 | 8/2009 | Speeg et al. | |
| 2010/0010341 A1 | 1/2010 | Talpade et al. | |
| 2010/0010342 A1 | 1/2010 | Burbank et al. | |
| 2010/0022672 A1 | 1/2010 | Yoshimura | |
| 2010/0030149 A1 * | 2/2010 | Carr, Jr. | A61B 5/6842 |
| | | | 604/116 |
| 2010/0049084 A1 | 2/2010 | Nock et al. | |
| 2010/0049085 A1 | 2/2010 | Nock et al. | |
| 2010/0094169 A1 | 4/2010 | Lubock et al. | |
| 2010/0106085 A1 * | 4/2010 | Perot | A61M 5/31591 |
| | | | 604/83 |
| 2010/0113920 A1 | 5/2010 | Foerster et al. | |
| 2010/0204570 A1 | 8/2010 | Lubock | |
| 2010/0298698 A1 * | 11/2010 | Burbank | A61B 19/54 |
| | | | 600/431 |
| 2010/0331668 A1 | 12/2010 | Ranpura | |
| 2011/0028836 A1 | 2/2011 | Ranpura et al. | |
| 2011/0071391 A1 | 3/2011 | Speeg | |
| 2011/0071424 A1 | 3/2011 | Nock et al. | |
| 2011/0071431 A1 | 3/2011 | Speeg et al. | |
| 2011/0098595 A1 | 4/2011 | Hibner | |
| 2011/0166448 A1 | 7/2011 | Jones et al. | |
| 2011/0184280 A1 | 7/2011 | Jones et al. | |
| 2011/0184449 A1 | 7/2011 | Lubock et al. | |
| 2011/0218433 A1 | 9/2011 | Speeg et al. | |
| 2012/0022369 A1 | 1/2012 | Chesbrough et al. | |
| 2012/0078092 A1 | 3/2012 | Jones et al. | |
| 2012/0078238 A1 | 3/2012 | Carr, Jr. | |
| 2012/0215230 A1 | 8/2012 | Lubock et al. | |
| 2013/0006286 A1 * | 1/2013 | Lavelle | A61B 17/3468 |
| | | | 606/185 |
| 2013/0144157 A1 | 6/2013 | Jones et al. | |
| 2013/0184562 A1 | 7/2013 | Talpade et al. | |
| 2013/0190616 A1 | 7/2013 | Casanova et al. | |
| 2013/0237912 A1 | 9/2013 | Speeg | |
| 2013/0281847 A1 * | 10/2013 | Jones | A61B 17/0057 |
| | | | 600/431 |
| 2014/0039542 A1 | 2/2014 | Trommeter et al. | |

\* cited by examiner

MARKER ELEMENT, DEVICE FOR MAKING A MARKER ELEMENT, AND METHOD FOR MAKING A MARKER ELEMENT

FIELD OF THE INVENTION

Aspects of the present invention relate to methods and devices for making a marker element and a marker element made thereby. More particularly, aspects of the invention pertain to a tissue marker, and a device and method for making a tissue marker within a delivery device, and a method for making and/or assembling a kit for marking a tissue location.

BACKGROUND OF THE INVENTION

Markers are often used in the medical field to indicate a location where tissue (e.g., from a tumor) has been collected from a patient. The marker, and therefore the tissue collection site, can be subsequently located using imaging techniques like x-ray, ultrasound, or magnetic resonance imaging (MRI).

A variety of markers and devices for marking a tissue location are available in the medical field. Typically the markers are pre-fabricated in an assortment of shapes and sizes, and then the markers are delivered to a tissue location using a delivery device.

For example, U.S. Pat. No. 6,575,991 describes a device for percutaneous marking of a lesion. The device includes a cannula and a stylet having a shaft and a base. In use, the stylet shaft extends through a guide passage and into the interior of the cannula, while the stylet base remains outside of the cannula. The device further includes a plunger configured to move the stylet within the cannula and eject a marker into a lesion site. The marker is pre-shaped prior to being loaded into a marker recess of the cannula. The marker has one of several shapes, including a spiral, star-burst, y-shape and horseshoe shape. However, because the marker is pre-fabricated outside of the cannula, it must be sized to slide within the inner passage. Therefore, the marker is not specially sized and shaped for a particular cannula, nor does the marker fit snugly into the end of the cannula, for example. The marker thus may slide within the cannula and slip out before it can be properly injected into a tissue site. In addition to having a potentially disadvantageous size, the shape of the marker may cause it to catch on or become tangled with the stylet, thereby preventing or interfering with the injection.

Another device for marking tissue within a human body is described in U.S. Pat. No. 6,228,055. The device includes a marker and an apparatus for delivering the marker to a location within the human tissue. The apparatus includes a tube that is guided to the tissue location. In one embodiment, a second region of the tube includes a forming die, which forms the marker into a predetermined shape, such as a helix. An important feature of this invention is the ability to use markers having a variety of shapes in order to identify different locations in a tissue. However, the markers are either prefabricated, then inserted into a lumen, or a special die is incorporated into each delivery device and used to form the marker. As such, unnecessary steps and components are required to make and use the device, so it is unnecessarily costly.

In general, markers that are prefabricated then inserted into a lumen or cannula according to methods of the related art are costly. These approaches typically require machining processes that are designed for very small parts with very tight tolerances, and both of those items tend to drive costs higher.

In addition, one way to prevent a marker from slipping out of an end of a device is to plug the end with a biocompatible substance, for example, bone wax. Another way to prevent the marker from slipping out is to use a spacer between the plastic hubs of the cannula and the stylet, so that, before use, the marker is able to move in between the bone wax and the stylet, but not outside of those bounds. When a doctor or other user is ready to deliver the marker, the spacer is removed and the marker and bone wax are then pushed into the patient. However, the use of bone wax introduces another foreign material into the tissue site, which may increase the risk of potential infections or adverse events.

There is a need in the art for a devices, kits and methods of making a marker element that is less costly than known devices and methods. In one aspect, the marker element should be formed within the delivery device so that it is uniquely shaped and sized for a particular device to provide seamless and reliable delivery of the marker element to a tissue location.

SUMMARY OF THE INVENTION

A device for forming a marker element, the device comprising: a tube having a longitudinal direction; a base element received in a first end of the tube; a wire receiving portion at a second end of the tube; a force applicator receivable within the second end of the tube, the force applicator being configured to apply force to a received wire in the longitudinal direction of the tube to deformably compress the received wire to a selected length relative to the longitudinal direction of the tube.

A kit for forming a marker element, the kit comprising: a tube having a longitudinal direction; a base element receivable in a first end of the tube; a wire receivable in a second end of the tube; a force applicator receivable within the second end of the tube, the force applicator being configured to apply a compression force to the wire in the longitudinal direction of the tube; and an actuator element receivable within the second end of the tube, the actuator element being configured to apply an actuation force to a marker element formed by compression of the wire.

A marker delivery device, comprising: a tube having a longitudinal direction; a marker element preformed within the tube, the marker element fixedly positioned near a first end of the tube; and an actuator element receivable in a second end of the tube, the actuator element configured to move the marker element from the first end of the tube into a tissue site.

A method of making a marker element, comprising: receiving a base element in a first end of a tube; receiving a wire in a second end of the tube; and applying a force to an end of the wire, wherein the wire is compressed in a longitudinal direction of the tube to a shape corresponding to a selected length and constrained in outer shape by the tube so as to form a marker element.

A method of making a kit for marking a tissue, comprising: receiving a base element in a second end of the tube; receiving a wire in a first end of the tube; applying a force to the wire at the first end of the tube using a force applicator, wherein the force compresses the wire to a predetermined length of the tube to form the marker element within the tube; removing the force applicator from the tube and removing the base element, wherein the marker element is fixed near the second end of the tube by a friction force greater than a weight of the marker element; providing an actuator element receivable in the first end of the tube; and packaging the actuator element, the tube and the marker element together in a sterile material.

Additional advantages and novel features in accordance with aspects of the invention will be set forth in part in the description that follows, and in part will become more apparent to those skilled in the art upon examination of the following or upon learning by practice thereof.

BRIEF DESCRIPTION OF THE DRAWINGS

Various example methods and apparatuses in accordance with aspects of the present invention will be described in detail, with reference to the following figures, wherein.

DETAILED DESCRIPTION

These and other features and advantages of this invention are described in, or are apparent from, the following detailed description of various example aspects.

Figure 1:
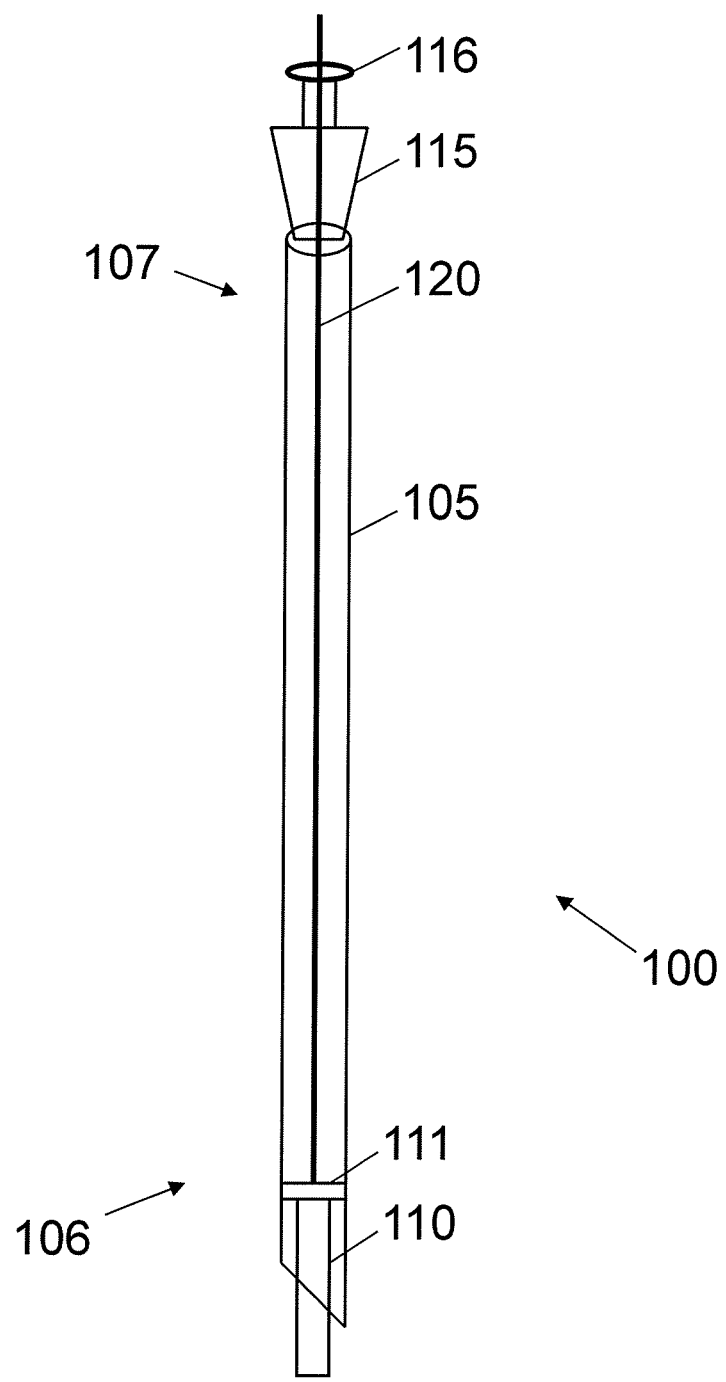
FIG. 1 illustrates aspects of an apparatus for making a marker element, according to various aspects of the present invention.

Referring to FIG. 1, in one aspect, the marker delivery apparatus 100 includes a tube 105 having a first end 106 and a second end 107. It should be noted that the terms "first end" and "second end" will be used consistently throughout the disclosure and claims to identify an end of an element (e.g., the wire 120, the base element 110, the force applicator 204, etc.) that is closest to the first end 106 or the second end 107, respectively. The tube may include, for example, a needle having a lumen, a cannula, or a trocar of any type suitable known for delivering a marker element or other items (e.g., a surgical device, medicaments) to a tissue site. In one aspect, an outer diameter of the tube is about the same or less than a diameter of a biopsy site.

The tube 105 may have a handle member 115 at the second end 107 for holding the tube 105. In one aspect, the handle member 115 includes an opening 116 in communication with the interior space of the tube 105, the opening 116 being configured to receive a wire 120 in a longitudinal direction of the tube 105. As will be described in more detail below, the wire 120 may be compressed to form a marker element.

In one aspect, the wire has a suitable length, diameter, malleability, tensile strength, yield strength, elongation properties and breakage properties to undergo compression to make the marker element. For example, the wire may have a length of about 1.5 inch to about 20 inch (e.g., 5 inch), a diameter of about 0.001 to 0.100 inch (e.g., about 0.006 inch), a tensile strength of about 18,000 to 25,000 psi (e.g., 21,000 psi), a yield strength of about 9,000 to 15,000 psi (e.g., 12,000 psi), an elongation at break of about 25% to 35% (e.g., 29%), and a breaking load of about 250 to 300 grams (e.g., 270 grams). The wire may also be in accordance with the chemical section of the ASTM-F-72 standard for gold.

The marker element may be formed from a wire having a high acoustic impedance compared to the tissue site and, optionally, may be radio-opaque. Suitable wire materials include, but are not limited to, biocompatible materials, such as gold, titanium, chromium, cobalt, stainless steel, silver, platinum, tantalum, palladium and alloys thereof. In one aspect, the wire may have a purity of 10K, 14K, 18K, 21K or 24K gold. Gold may be particularly be useful as a marker material for some applications of the technology because it is visible by imaging techniques, such as x-ray, ultrasound, or MRI, and is highly bio-compatible. Gold is also useful because it provides a smaller MRI artifact, which aids physicians in viewing the area directly around the marker. Other metals may have larger artifacts and may obscure areas directly around the marker. Additionally, composite materials, including one or more of the aforementioned metals and a polymer, for example, polyetherketoneketone, polyethylene, polypropylene, polyurethane, polytetrafluoroethylene, polyvinyl-chloride, polyamides, and polycarbonate may also be used to form the compressible, malleable wire 120. In other aspects, the wire 120 may include one or more of the aforementioned polymers.

In other aspects, the wire 120 may have a cross-section that is circular, ovular, rectangular, triangular, trapezoidal, or any other polygonal shape (e.g., star-shaped). The wire 120 may also be braided, twisted, flat or of any other shape or configuration suitable for compression within the tube to form a marker element. Moreover, the cross-section, shape and/or configuration of the wire 120 may be selected to optimize bending of the wire and formation of the marker element.

A base element 110 may be configured for insertion into the first end 106 of tube 105 as shown in FIG. 1. The base element 110 may be constructed of any suitable material, for example, a polymer, a metal or a combination of the two. In one aspect, the base element 110 may include an end element 111 configured to seal the first end 106 of the tube 105 and to provide a base against which the wire 120 is compressed. If an end element 111 is not incorporated, the base element 110 may be sized slightly smaller (e.g. about 0.0001 to about 0.001 inch) than the inner diameter of the tube 105, so that it is able to be slidably received within the tube 105. In another aspect, the base element 111 may comprise a soft material, such as silicone, rubber, or other polymer that is configured to slightly deform during compression of the wire 120 and formation of the marker element.

Figure 2:
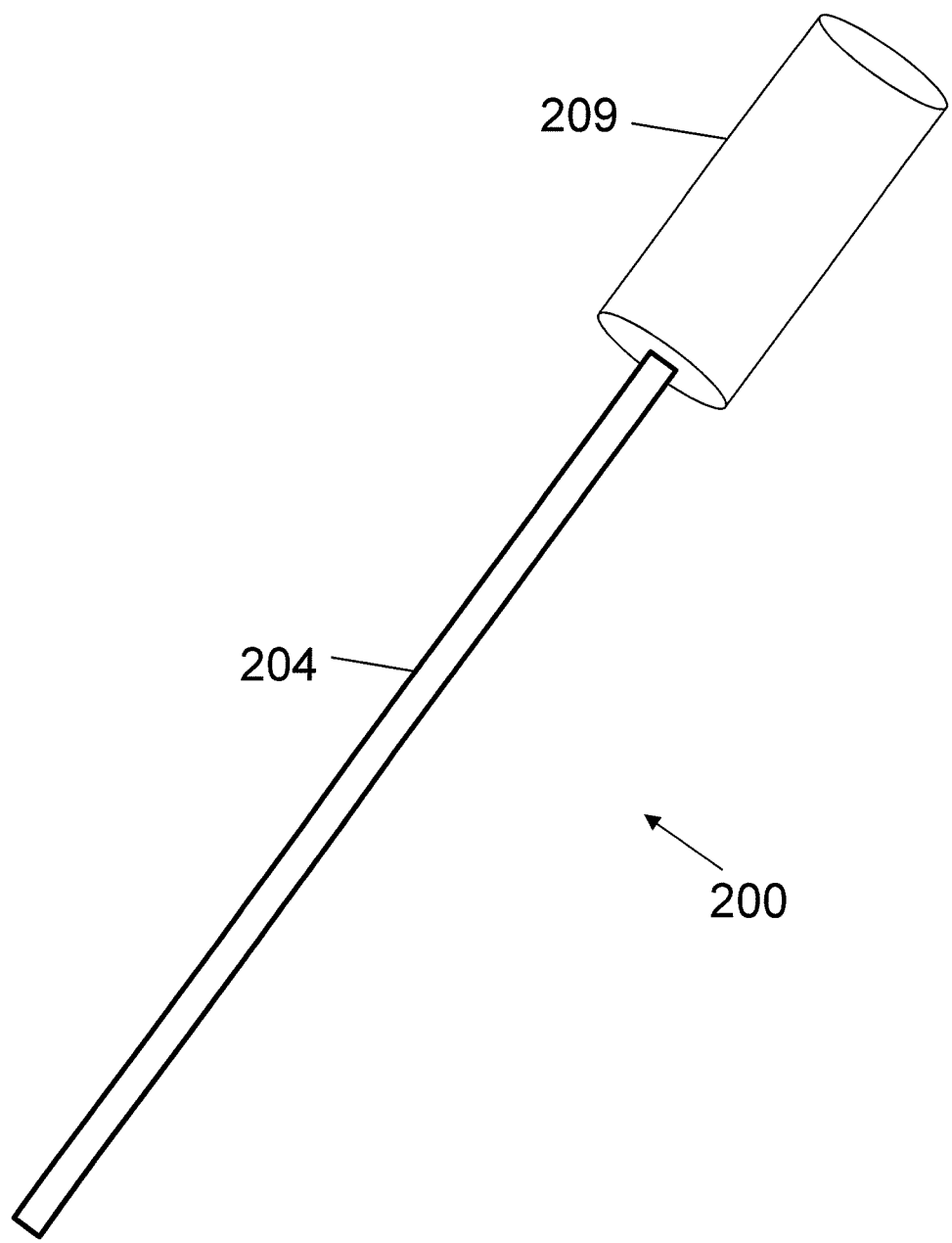
FIG. 2 illustrates aspects of an apparatus for making a marker element, according to various aspects of the present invention.

A force applicator 204, (e.g., a rod), may be used to compress (or crumple, for example) the wire 120 within the tube 105. An example of such a force applicator 204 is shown in FIG. 2. In one example aspect, the force applicator 204 may have a handle element 209 at a second end for gripping or holding the force applicator 204. The handle element 209 may also be in communication with an electrically driven press (not shown), hydraulic mechanism (not shown) or other compression mechanism configured to move the force applicator 204 in and out of the inside portion of the tube 105, as would be readily understood by those of skill in the art. As will be described in more detail below, the force applicator 204 may be configured to compress the wire 120 to a selected length of the tube, for example, so that the compressed wire 120 (i.e., the resulting marker element) is about 3 mm as measured between the a second end of the base element 110, 111 and a first end of the force applicator 204, thereby forming the marker element. In various aspects, the force applicator 204 may be formed of a metal or a polymer material, or a combination thereof. The force applicator 204 may need to have a sufficient hardness to compress the wire 120 without breaking.

In another aspect, the force applicator 204 may have a similar shape to the tube 105, and the size of the force applicator 204 may be such that when inserted into the tube 105, there is a clearance of about 0.0005 to about 0.003 inches, preferably about 0.001 to about 0.002 inches, between the outside surface of the force applicator 204 and the inside surface of the tube 205. For example, if the tube 105 is cylindrical and the force applicator 204 is cylindrical, the diameter of the force applicator 204 may also be about 0.001 to about 0.002 inches smaller than the inside diameter of the tube 105. If the tube 105 and force applicator 204 have an elliptical cross-section, for example, then the clearance between the outside surface of the force applicator 204 and the inside surface of the tube 105 may be about 0.001 to about 0.002 inches. This clearance ensures adequate compression of the wire 120 and optimal formation of the marker, as will be further explained below. Moreover, the clearance should generally not be too small, or the force applicator 204 may not be readily moveable within the tube 105. Also the force applicator 204 generally should not be too great, or it will not compress the wire 120 from its second end (e.g., the force applicator 204 may slip to one side or another of the wire 120). Therefore, the inventors have found that a force applicator 204 sized so that there is a clearance of about 0.001 to about 0.002 inches is particularly useful for compression of the wire 120 for some applications of the technology.

Figure 3:
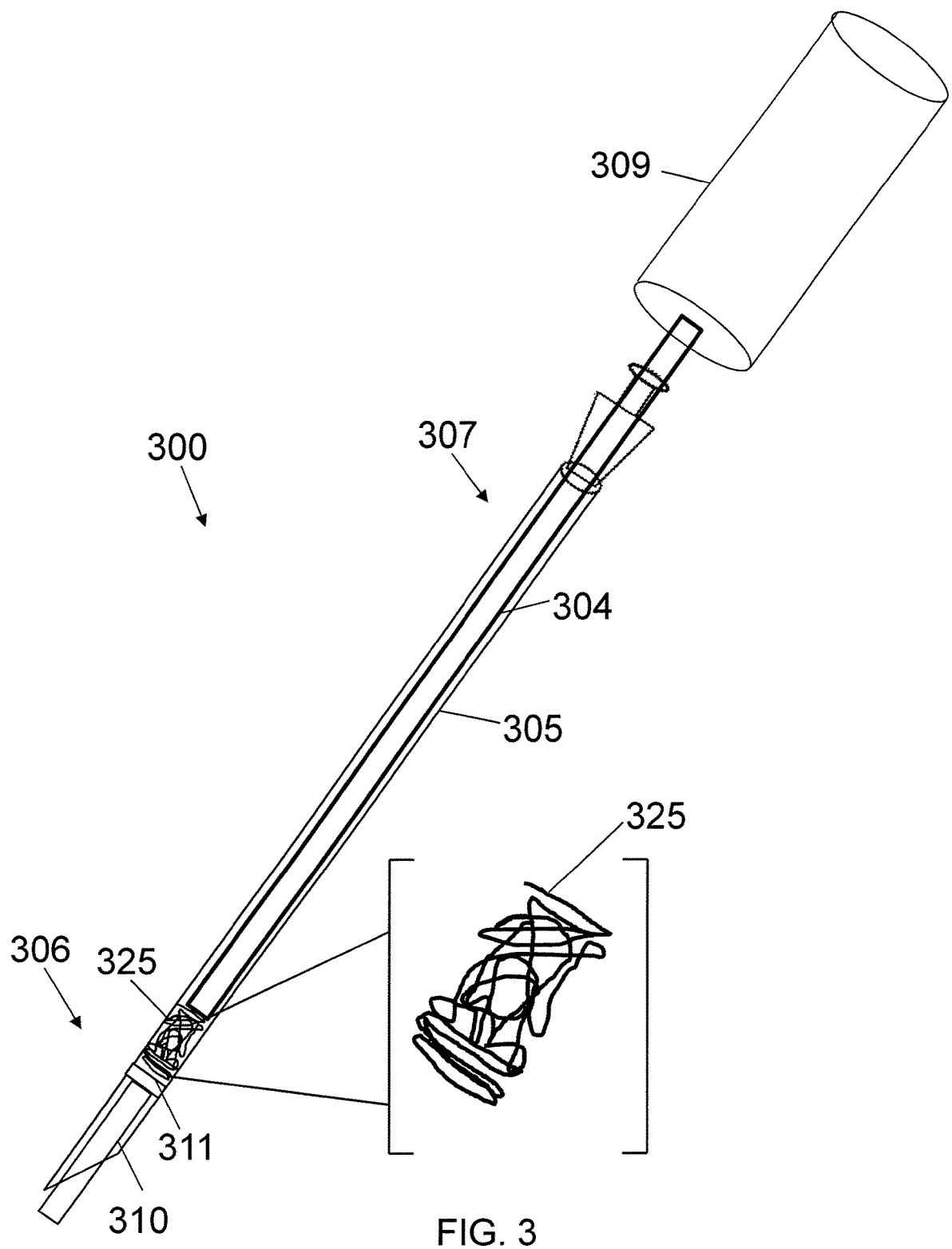
FIG. 3 illustrates aspects of an apparatus for making a marker element, according to various aspects of the present invention.

In FIG. 3 the force applicator 304 is shown inserted into the tube 305 after compressing the wire to a predetermined length of the tube 305, so as to form the marker element 325. As will be appreciated by those of ordinary skill in the art, a marker element 325 formed in a particular tube 305 may differ from another marker element 325 formed in a different tube 305, even though the wire and tube may be of the same or similar size and material. Thus, because of 1) the mechanical properties of each wire 120 used to form the marker element 325, 2) the relative size of the wire 120 to the tube 305, and 3) the physical placement or location of the wire 120 within the tube 305 prior to compression, a first marker element formed in a first tube, may differ from a second marker element formed in a second tube. As will be appreciated by those skilled in the art, for example, a first wire will not bend in exactly the same manner as a second wire when undergoing compression by the force applicator 304 in a first tube as compared to a second tube. For example, if a first wire is placed close to an inside surface of a first tube and a second wire is placed in the middle of a second tube, this placement will affect how the wire bends. It is an aspect of the present invention that such placement does not need to be controlled, which reduces the time and cost associated with forming a marker element 325.

The marker element 325 depicted in FIG. 3 is just one example of how the wire 120 may bend from compression by the force applicator 304 to form the marker 325. In one aspect, the first end of the wire 120 may initially coil during compression and at the end of compression, for example, the second end of the wire 120 may be compressed flat. While multiple marker elements 325 formed using a method and/or apparatus in accordance with aspects of the present invention may differ, all marker elements 325 (e.g., 325a, 325b, etc.) formed in respective tubes 305 (e.g., 305a, 305b) may have common characteristics. For example, a marker element 325 may be about 2 mm to about 5 mm in length, preferably about 3 mm in length, as measured between the second end of the base element 110, 111 (i.e., the inside face of end element 111) and the first end of the force applicator 304. More specifically, the force applicator 304 may be sized so that it will stop compression of the wire when the first end of the force applicator 304 is at a predetermined distance from the second end of the base element 110.

A positive stop may be provided between the applicator and the fixture. In this case, the handle of the applicator may be sized such that it encompasses or partially encompasses the receiving element 406 and contacts the fixture so that it cannot be pushed down any further. At the point of contact, the applicator rod may be in the appropriate position to create a marker of the desired size.

A control mechanism, electronic or hydraulic, for example, may be provided, where the travel of the applicator is monitored by a feedback loop, and, when the applicator travels the prescribed distance to create a marker of a certain size, the control mechanism stops the travel of the applicator and returns it to the home position.

Moreover, a total mass of wire used to form a particular marker element 325 (e.g., 325a, 325b) may be the same or similar for each particular marker element 325 formed by the method and apparatus of the present invention. For example, an 18 gauge, 18 karat gold wire may have a length of about 10 inches and a 12 gauge, 18 karat gold wire may have a length of about 2.5 inches, the total mass of marker element 325 produced from each wire is approximately the same. In one example aspect, the total mass of wire received to form the marker element may be about 1 g to about 10 g (e.g., about 4 g).

In addition, the resulting marker element 325 may have a general shape consistent with the inside shape of the tube 305. For example, in the case of a cylindrical tube, the resulting marker element 325 may be generally cylindrical in shape. It will be appreciated that during longitudinal compression, the wire may bend in a radial direction, as well. Thus, during compression, the wire may exert a force against the inside surface of the tube 305 so that the resulting marker element 325 is shaped and sized to fit snuggly within the particular tube 305 and is held in place near the first end 306 of the tube 305. Thus, when the base element 310, 311 and force applicator 304 are removed, the marker element 325 may remain in place. For example, the friction force required to move the marker element 325 in the tube 305 may be greater than the weight of the marker element 325, which prevents undesired sliding of the marker element within the tube 305.

Another characteristic of the marker element 325 may be the formation of open spaces within the general structure as a result of the random bending of the wire. For example, as shown in FIG. 3, the wire may be compressed to form a generally cylindrical structure having open spaces formed between the bends in the wire. Therefore, when implanted in a tissue, the open spaces of the marker element 325 may be filled by growing tissue, which ensures the marker element 325 will remain in place.

In other aspects, the size of tube 305 (e.g., length and diameter) may differ between one patient and another, depending, for example, on the type of procedure, location of tissue extraction, size of the patient and/or weight of the patient. Therefore, the length and diameter of the force applicator 304 may also differ, depending on the circumstances. Nonetheless, the marker element 325 may generally be about 2 mm to about 5 mm in length, preferably about 3 mm in length, and the force applicator 304 may be sized to have a clearance of about 0.0005 to 0.003 inch, preferably about 0.001 to 0.002 inches, between its outer surface and the inner surface of the tube 305. It should be noted that the depiction of the force applicator 304 in tube 305 in FIG. 3 is merely for illustrative purposes. In one aspect, the outside diameter of the force applicator 304 may be very proximally close to the inner surface of the tube 304, for example, when the clearance is 0.0005 to 0.003 inch. In addition, the resulting marker element 325 may have the same or similar characteristics to as described above.

Figure 4:
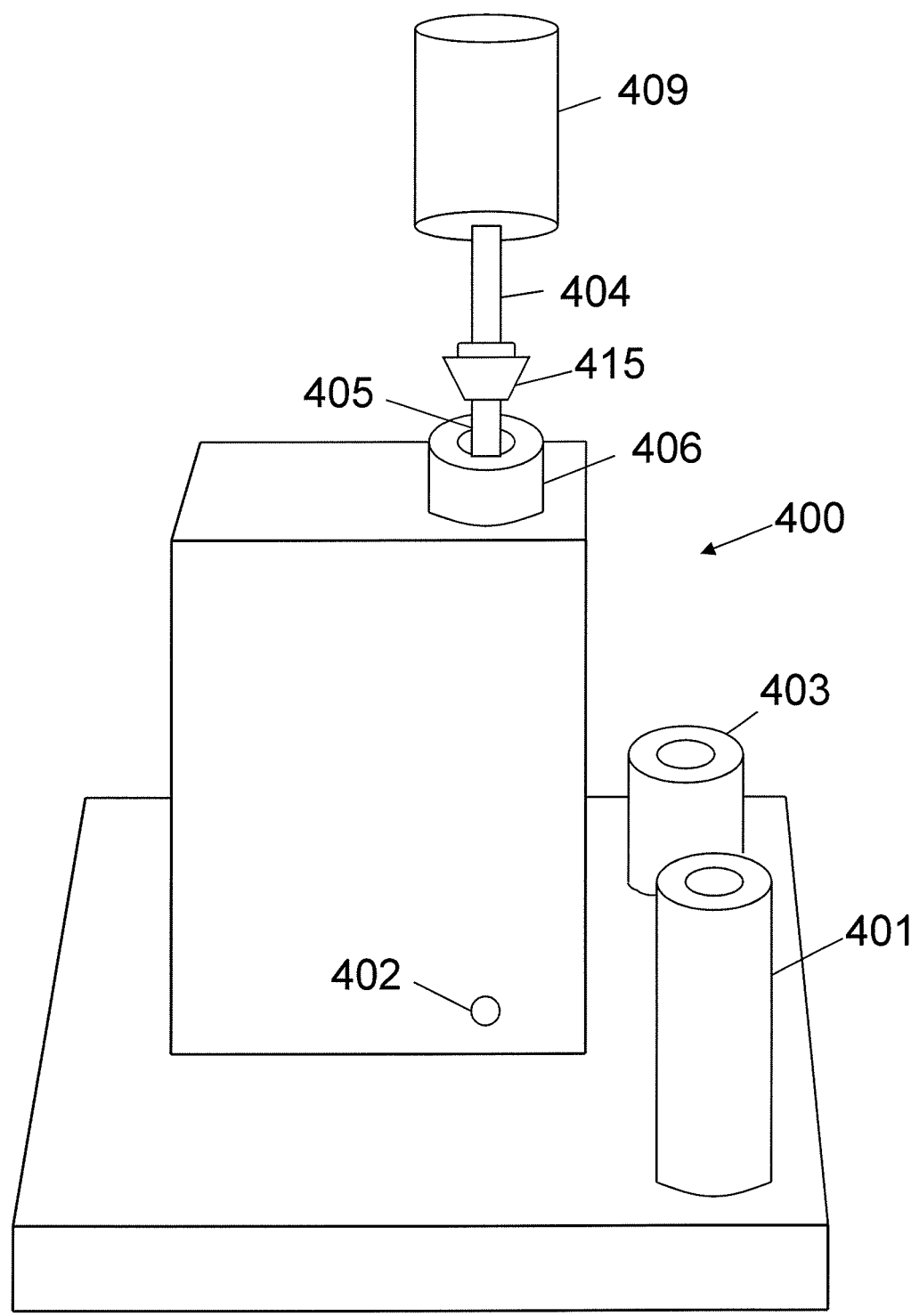
FIG. 4 illustrates aspects of an apparatus for making a marker element, according to various aspects of the present invention.

In other aspects of the invention, a fixture 401 may be used to aid in the compression of the marker element, as shown in FIG. 4. A tube 405 may be inserted into the fixture 400 having incorporated therein a base element (not shown in FIG. 4) that is movable in and out of the first end (not shown in FIG. 4) of the tube 405 via an element 402, such as a set screw, located at a base of the fixture 400. In one aspect, element 402 holds the base element in place. If the base of the fixture 401 is removable for access to the base element. In some variations, the height of the base element may then be adjusted by loosening the screw and moving the base element up or down a certain amount. When the desired height is reached, the screw may be tightened again, such as to hold the base element in place.

In an example aspect, the fixture 400 may be configured to hold the tube 405 vertically as shown in FIG. 4. Vertically orienting tube 405 may provide for easier manufacturing, for example, in that the first end of wire 120 may be inserted through the second end of tube 405, and then released, such that gravity pulls wire 120 down until it contacts the base element. A horizontally oriented fixture would not provide similar manufacturing ease. The force applicator 404 may then be inserted into the tube 405 to compress the wire (not shown) and form the marker element (not shown). The fixture 400 may include extender elements 401, 403, for example, that may be affixed to the receiving element 406 of the fixture 400, where the extender elements 401, 403 are used to hold longer tubes 405. Consequently, longer force applicators 404 may also be used.

In another aspect, the fixture shown in FIG. 4 may create one marker element at a time; however, a larger scale fixture may also be used. A larger scale fixture may be configured to hold multiple tubes, for example. In another example for an automated process, the larger scale fixture may be moveable beneath a force applicator or multiple force applicators. When aligned with a tube, the force applicator(s) may be lowered to compress the corresponding wire(s) and then raised to remove the force applicator(s) from the tube(s). After compression in a first tube, the fixture may then translate one space, for example, so that a second tube may be aligned with the force applicator for compression.

It should be noted that the length of the force applicator 204, 304, 404 may be sized to stop compression at a predetermined length of the tube 105, 305, 405 to form the marker element (e.g., the force applicator may be shorter than the tube). In this instance, the base element 110, 111 may be sized to slide into a first end 106 of the tube at a (repeatable) predetermined length (e.g., so that there is a predetermined length between the end of the force applicator and the base element).

Although the force applicator 304, 404 may be manually pushed into tube 305, 405 using handle 309, 409 to form the marker element, in one aspect, a compression mechanism (e.g., an electrically driven press or hydraulic mechanism) may be used. In an automated process, a robot or other mechanism employed to lower the force applicator, may be controlled based on, for example, the lowering rate of the force applicator and elapsed time, a detection sensor or sensors configured to detect height, or by any other suitable means known to those of skill in the mechanical processing arts.

Figure 5:
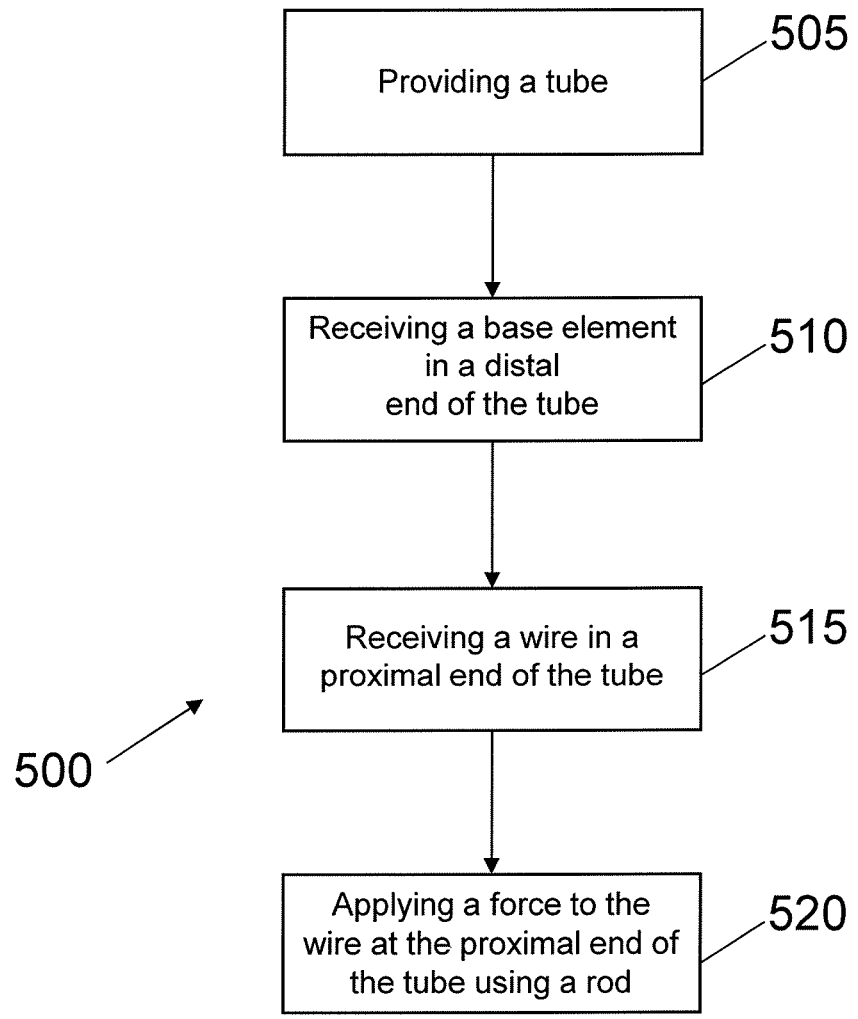
FIG. 5 provides a flow chart of a method for making a marker element within a marker delivery apparatus, according to various aspects of the present invention.

Aspects of a method of making a marker element 500 according to the present invention are described with reference to FIG. 5. The method 500 may optionally include, at 505 providing a tube (e.g., tube 105, 305, 405 as described in reference to FIGS. 1, 3 and 4 above). In one aspect, at 505 providing the tube comprises receiving the tube in a fixture (e.g., 400 of FIG. 4) for supporting the tube. The fixture may be configured to support the tube in a vertical orientation, for example, as shown in FIG. 4. In another aspect, the base element (e.g., element 110, 310 of FIGS. 1, 3) may be coupled to an element of the fixture.

The method may further include at 510 receiving a base element (e.g., element 110, 310 of FIGS. 1, 3) in a first end (e.g., end 106, 306 of FIGS. 1, 3) of a tube, where the base element seals the first end of the tube and provides a base against which the wire (e.g., wire 120, 320 of FIGS. 1, 3) is compressed. The base element may be configured to position a second end of the wire at a predetermined position near the first end of the tube, for example.

At 515, the method includes receiving a wire in a second end of the tube, where the wire is as described above with reference to FIGS. 1 and 3, for example. The wire may be on a spool and inserted into the second end of the tube while still on the spool, for example. The wire may then be cut to a selected length so that the density of wire used to make, for example, a first marker element and a second marker element that is the same or very similar. The wire may also be cut to different lengths, for example, to create a first marker element and a second marker element having densities that are significantly different. In one aspect, the spool may be automated to dispense and cut the wire to a predetermined length. In another aspect, the wire may be cut to a selected length before insertion into the tube. As discussed with respect to FIG. 1, the wire may be malleable and comprise a suitable material resistant to foreign body reactions. In example aspects, the wire may be gold, and, particularly for some applications of the technology, annealed gold.

At 520, the method includes applying a force to a second end of the wire using a force applicator, wherein the force compresses the wire in a longitudinal direction of the tube to a predetermined length of the tube to form the marker element within the tube. In one aspect, the width or diameter of the force applicator may be less than an inner width or diameter of the tube so as to provide clearance, as discussed above with reference to FIGS. 1 and 3. In another aspect, the width or diameter of the force applicator may be greater than the width or diameter of the wire. Applying a force at 512 may further include one or more of moving a device coupled to the force applicator, activating an electrically driven mechanism configured to move the force applicator, and/or activating a hydraulic mechanism configured to move the force applicator.

Aspects of a method of making or assembling a kit for marking a tissue are described with reference to FIG. 6. Like the method 500 of FIG. 5, method 600 of FIG. 6 includes providing a tube 605 (optionally), receiving a base element in a first end of the tube 610, receiving a wire in a second end of the tube 615, applying a force to the wire at the second end of the tube using a force applicator, wherein the force compresses the wire to a predetermined length of the tube to form the marker element within the tube 620, and removing the force applicator from the tube 625.

In other aspects, method 600 may include at 625 removing the base element from the tube. In one aspect, after compression and removal of the base element, the marker element may remain fixed near the first end of the tube such as by a friction force greater than a weight of the marker element.

Figure 6:
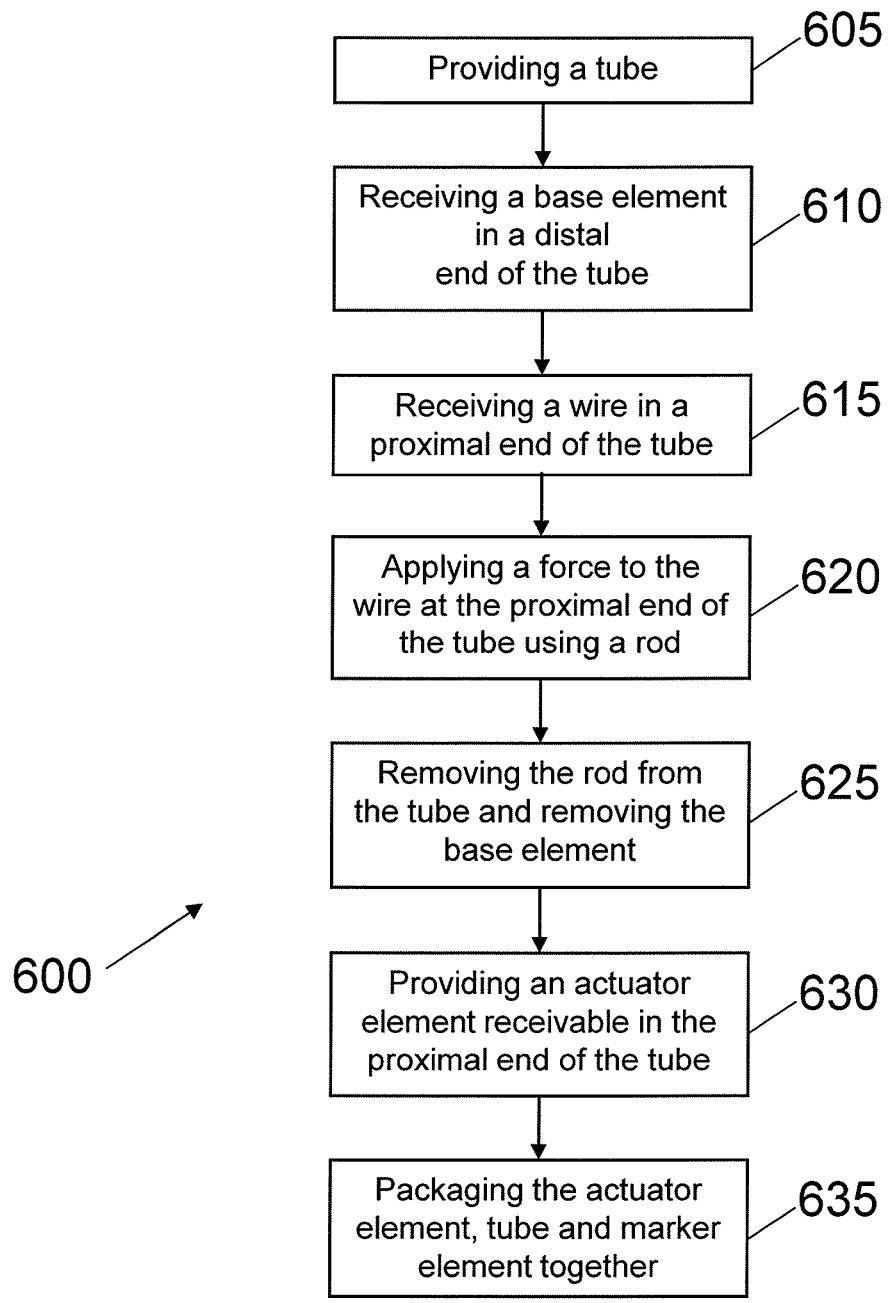
FIG. 6 provides a flow chart of a method for making a marker element within a marker delivery apparatus, according to various aspects of the present invention.
Figure 7:
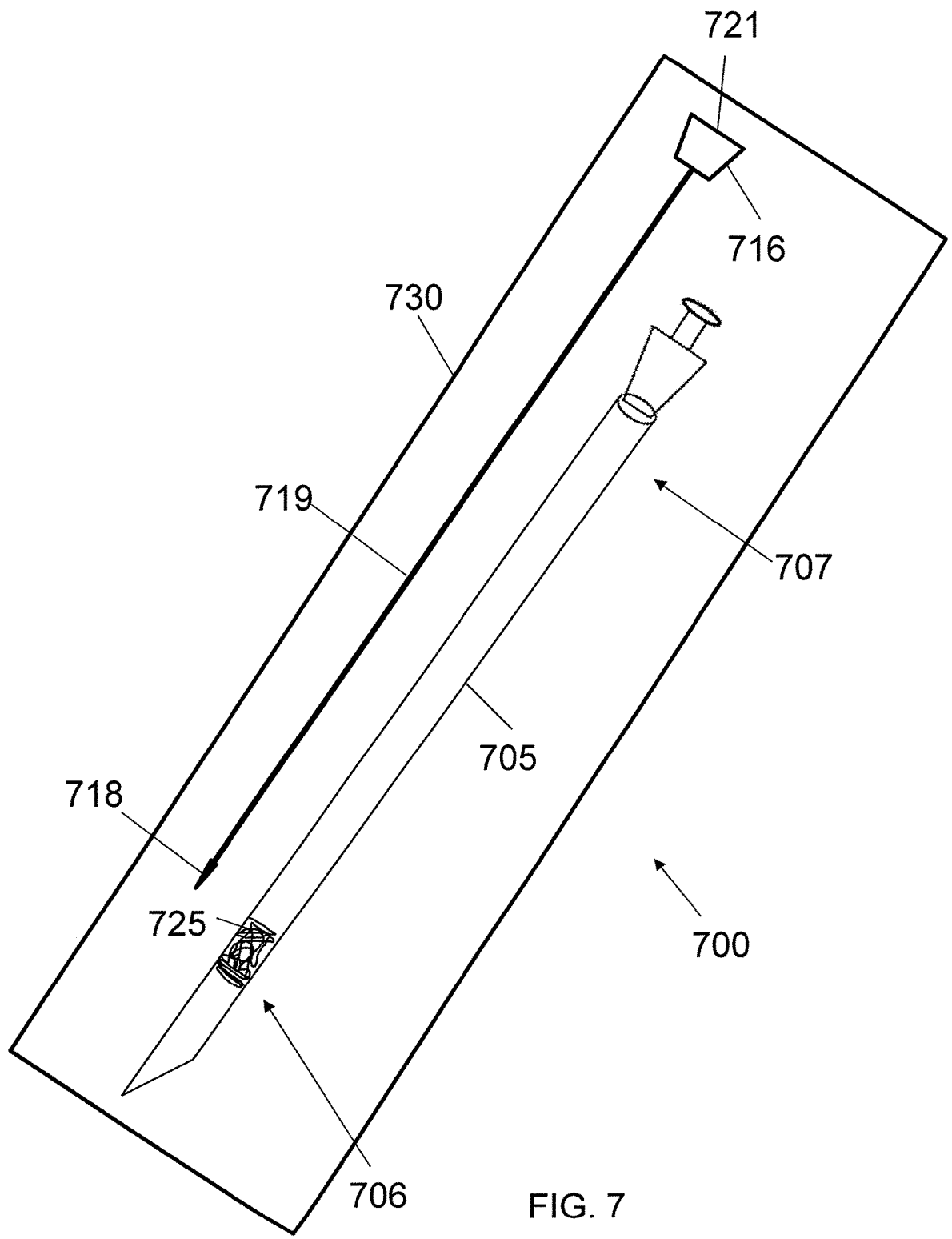
FIG. 7 illustrates aspects of a kit for delivering a marker element to a tissue, according to various aspect of the present invention.

With reference to the method of FIG. 6 as applicable to the example kit of FIG. 7, at 630, the method 600 includes providing an actuator element (e.g., element 719 of FIG. 7) receivable in the second end 707 of the tube 705. In one aspect, a first end of the actuator element 719 may form a sharp tip 718, like a needle or stylet, which may assist in moving the marker element 725 from the tube 705 and into a tissue site (not shown). In another aspect, the tip may be flat (not shown). In yet another aspect, the actuator element, like the force applicator (discussed above), is sized so that there is a clearance of about 0.0005 to about 0.003 inch (e.g., about 0.001 to 0.002 inch) between the outer diameter of the actuator element and the inner diameter of the tube. In addition, the tissue site may be or include the site of a biopsy or surgical incision.

In another aspect, method 600 as applied to the kit of FIG. 7 may further include at packaging the actuator element 719, the tube 705 and the marker element 725 together in a sterile material 730 to form a kit 700. The sterile material 730 may be any suitable material that is typically used for packaging sterile equipment used in the medical field, for example.

While aspects of this invention have been described in conjunction with the example features outlined above, various alternatives, modifications, variations, improvements, and/or substantial equivalents, whether known or that are or may be presently unforeseen, may become apparent to those having at least ordinary skill in the art. Accordingly, the example aspects of the invention, as set forth above, are intended to be illustrative, not limiting. Various changes may be made without departing from the spirit and thereof. Therefore, aspects of the invention are intended to embrace all known or later-developed alternatives, modifications, variations, improvements, and/or substantial equivalents.

What is claimed is:

1. A device for forming a marker element, the device comprising:
    a tube having a longitudinal direction, the tube configured to deliver a marker element into a patient;
    a base element having a shape configured to be receivable in a first end of the tube, the base element secured in the tube, thereby sealing the tube;
    an opening at a second end of the tube configured to receive a wire;
    a force applicator comprising a longitudinal first end having a shape configured to be receivable within the second end of the tube, the force applicator being configured to apply a force to a received wire in the longitudinal direction of the tube to compress the received wire,
    wherein the force is sufficient to deformably compress the received wire against the base element to a selected length relative to the longitudinal direction of the tube in order to form the marker element inside the tube,
    wherein the base element is configured to remain secured as the force is applied,
    wherein the location of the base element is adjustable relative to the first end of the tube, and
    wherein the force applicator is sized to stop compression of the received wire at a predetermined distance from the base.

2. The device of claim 1, wherein an outer diameter of the tube is the same or less than a diameter of a biopsy site in which the marker element is to be emplaced.

3. The device of claim 1, comprising a separable fixture comprising a cylinder configured to receive the tube.

4. The device of claim 3, wherein the fixture comprises a base section coupled to the cylinder, wherein the base section is configured to support the cylinder in a vertical orientation so that the second end of the tube is configured to protrude from a top end of the cylinder.

5. The device of claim 3, wherein the base element is directly coupled to the fixture.

6. The device of claim 1, wherein the base element is configured to position an end of the received wire near the first end of the tube.

7. The device of claim 1, wherein the base element is configured to position the end of the received wire 2 to 5 mm from the first end of the tube.

8. The device of claim 1, wherein a clearance between an outer diameter of the force applicator and an inner diameter of the tube is 0.0005 to 0.003 inches.

9. The device of claim 8, wherein a clearance between an outer diameter of the force applicator and an inner diameter of the tube is 0.001 to 0.002 inches.

10. The device of claim 1, wherein the marker element is constrained to one or more dimensions within the tube so as to be constrained between the base element and an end of the force applicator.

11. The device of claim 10, wherein the constrained length of the marker element is 2 to 5 mm.

12. The device of claim 11, wherein the constrained length of the marker element is 3 mm.

13. The device of claim 1, wherein the marker element has an outer shape limited by a shape of an inner surface of the tube.

14. The device of claim 1, wherein the marker element comprises a plurality of open spaces configured to receive tissue in-growth.

15. The device of claim 1, wherein the marker element has a cylindrical outer surface shape with a plurality of open spaces.

16. The device of claim 1, wherein the marker element comprises a mass of total received wire of 1 g to 10 g.

17. The device of claim 1, wherein the marker element exerts a force against an inner surface of the tube.

18. A kit for forming a marker element, the kit comprising:
    a tube having a longitudinal direction, the tube configured to deliver a marker element into a patient;
    a base element having a shape configured to be receivable in a first end of the tube, the base element secured in the tube, thereby sealing the tube;
    a wire receivable in a second end of the tube;
    a force applicator comprising a longitudinal first end having a shape configured to be receivable within the second end of the tube, the force applicator being configured to apply a compression force,
    wherein the compression force is sufficient to compress the wire in the longitudinal direction of the tube against the base element in order to form the marker element inside the tube, wherein the base element is configured to remain secured as the compression force is applied, and wherein the force applicator is configured to stop compression of the wire at a distance from the first end of the tube sufficient to cause the marker element to remain within the tube; and a stylet receivable within the second end of the tube, the stylet being configured to apply an actuation force to move the marker element formed by compression of the wire from the tube.

19. The kit of claim 18, comprising a separable fixture comprising a cylinder configured to receive the tube.

20. The kit of claim 18, wherein the base element is configured to position an end of the wire near the first end of the tube.

21. The kit of claim 18, wherein the wire comprises a metal selected from a group consisting of gold, titanium, chromium, cobalt, stainless steel, silver, platinum, tantalum and alloys thereof.

22. The kit of claim 18, wherein the wire comprises annealed gold.

23. The kit of claim 18, wherein the wire has a length of 1.5 to 20 inches, a diameter of 0.004 to 0.100 inches, a tensile strength of 18,000 to 25,000 psi, a yield strength of 9,000 to 15,000 psi, an elongation at break of 25% to 35%, and a breaking load of 250 to 300 grams.

24. The kit of claim 18, wherein the base element when received in the tube is configured to position an end of the wire at a predetermined length from the first end of the tube and wherein the force applicator is configured to stop compression of the wire at a predetermined distance from the base element.

25. The kit of claim 24, wherein the predetermined distance is 3 mm.

26. The kit of claim 18, wherein the stylet is configured to move the marker element from the tube and into a tissue site.

27. The kit of claim 18, wherein the marker element exerts a force against an inner surface of the tube.

28. A marker delivery device, comprising:

a tube having a longitudinal direction, the tube configured to deliver a marker element into a patient;

the marker element preformed within the tube, the marker element fixedly positioned near a first end of the tube; and a stylet receivable in a second end of the tube, the stylet configured to move the marker element from the first end of the tube into a tissue site, wherein the tube is configured to receive a base element having a shape configured to be receivable in the first end of the tube to form a base on which the marker element is preformed, wherein the base element is secured in the tube, thereby sealing the tube, and is configured to remain secured as the marker element is preformed within the tube by a force sufficient to advance a deformably compressible wire in the longitudinal direction of the tube against the base element, and wherein the base element is secured in the tube by a force independent of the tube.

29. The device of claim 28, wherein the tube is configured to receive the deform ably compressible wire in the second end of the tube, an inner surface of the tube being configured to exert an opposing force against the wire during compression of the wire to shape the wire and thereby preform the marker element.

30. The device of claim 28, wherein the tube is configured to receive a force applicator in the second end of the tube, the force applicator being configured to apply the force in order to compress the wire to preform the marker element within the tube.

31. The device of claim 28, wherein the tube is configured to receive a base element in the first end of the tube, the wire in the second end of the tube and a force applicator in the second end of the tube, wherein the force applicator is configured to compress the wire between the base element and the force applicator to preform the marker element.

32. The device of claim 28, wherein the marker element is preformed to a length and dimensions within the tube between the base element and the force applicator.

33. The device of claim 28, wherein the marker element exerts a force against an inner surface of the tube.

34. A method of making a marker element, comprising:

receiving an empty tube;

receiving a base element in a first end of the tube, wherein the base element has a shape configured to be receivable in the first end of the tube and is secured in the tube, thereby sealing the tube;

receiving a wire in the tube through an opening at a second end of the tube;

applying a force to an end of the wire, wherein the force is sufficient to compress the wire in the longitudinal direction of the tube against the base element in order to form a marker element inside the tube, wherein the marker element exerts a force against an inner surface of the tube, and wherein the base element remains secured in the tube as the force is applied and the wire is compressed in a longitudinal direction of the tube against the base element to a shape corresponding to a selected length and constrained in outer shape by the tube so as to form the marker element; and removing the base element from the first end of the tube after the marker element is formed and prior to insertion of the tube into a patient, wherein the marker element is retained within the tube via the force against an inner surface of the tube after the base element is removed.

35. The method of claim 34, wherein a clearance between an outer diameter of the force applicator and an inner diameter of the tube is 0.001 to 0.002 inches.

36. The method of claim 34, wherein applying the force comprises activating a compression mechanism selected from the group consisting of a lever coupled to the force applicator, an electrically driven press and a hydraulic mechanism, wherein the compression mechanism is configured to move the force applicator.

* * * * *